United States Patent [19]

Yamamoto et al.

[11] Patent Number: 5,281,580
[45] Date of Patent: Jan. 25, 1994

[54] CALCITONIN-CONTAINING EMULSION FOR NASAL ADMINISTRATION

[75] Inventors: Nakayuki Yamamoto, Shizuoka; Michihiko Sugimoto, Numazu; Hideo Sakakibara, Mishima; Masaru Saita, Saga; Yuji Shimozono, Tosu; Takafumi Manako, Saga, all of Japan

[73] Assignees: Toyo Jozo Company, Ltd.; Hisamitsu Pharmaceutical Co., Inc., Saga, Japan

[21] Appl. No.: 734,637

[22] Filed: Jul. 23, 1991

[30] Foreign Application Priority Data

Aug. 16, 1990 [JP] Japan ................... 2-215044

[51] Int. Cl.⁵ .............. A61K 33/24; A61K 9/06; A61K 37/30; C07K 7/36
[52] U.S. Cl. ................. 514/12; 514/11; 514/808
[58] Field of Search .............. 514/12, 808, 11

[56] References Cited

U.S. PATENT DOCUMENTS

| | | | |
|---|---|---|---|
| 4,690,852 | 9/1987 | Katagani et al. | 514/2 |
| 4,835,132 | 5/1989 | Suzuki et al. | 514/180 |
| 4,882,359 | 11/1989 | Nakagawa et al. | |
| 5,026,825 | 6/1991 | Grebow et al. | 530/307 |

FOREIGN PATENT DOCUMENTS

| | | |
|---|---|---|
| 115627 | 8/1984 | European Pat. Off. |
| 0183527 | 4/1986 | European Pat. Off. |
| 0358234 | 3/1990 | European Pat. Off. |
| 2127689 | 4/1984 | United Kingdom |
| 2212062 | 7/1989 | United Kingdom |

OTHER PUBLICATIONS

Chemical Abstracts, vol. 110, No. 16, Apr. 17, 1989, Columbus Ohio, USA N. Yamamoto et al. "Intranasal compositions containing calcitonins or parathyroid hormones" p. 414 589a & Jpn. Kokai Tokkyo Koho JP 63,243,033 (88,243,033).

Patent Abstracts of Japan, unexamined applications, section C, vol. 12, No. 110, Apr. 8, 1988 The Patent Office Japanese Government p. 159 C 486 *Kokai-no. 62-238 261 (Hisamitsu Pharmaceut Co Inc.)*.

Chemical Abstracts, vol. 105, No. 18, Nov. 3, 1986, Columbus, Ohio, USA T. Hasumi et al. "Nasal formulations containing calcitonin and amino acids" p. 375, col. 2, abstract no. 158 833v & Jpn. Kokai Tokyo Koho JP 61,118,325 (86,118,325).

Chemical Abstracts, vol. 109, No. 22, Nov. 28, 1988, Columbus, Ohio, USA T. Hasumi et al. "Nasal compositions containing calcitonin" p. 456, col. 2, abstract-no. 197 195r & Jpn. Kokai Tokkyo Koho JP 63 10, 735 (88 10,735).

Japanese Publication 3-83925.
Japanese Publication 3-83926.
Delivery System for Peptide Drugs, Plenum Press, 233-242, 1986.

Primary Examiner—Howard E. Schain
Assistant Examiner—P. Lynn Touzeau
Attorney, Agent, or Firm—Wyatt, Gerber, Burke and Badie

[57] ABSTRACT

The present invention is to provide emulsion preparations for nasal administration containing calcitonins, which are safely and effectively administrated, compared with the conventional calcitonin preparations. The emulsions are prepared by using a calcitonin as the active ingredient, an azacycloalkane derivative as the absorption promotor such as 1-[2-(decylthio)ethyl]azacyclopentan-2-one, and glycyrrhizic acid or its salt.

6 Claims, 2 Drawing Sheets

CALCITONIN-CONTAINING EMULSION FOR NASAL ADMINISTRATION

The present invention relates to an emulsion for nasal administration containing a calcitonin as the active ingredient. Particularly, it relates to such emulsion for nasal administration, having superior stability, and being so improved that the calcitonin is absorbed safely and efficiently spraying administration in the nasal cavity.

Progressive development has been effected in the use of physiologically active peptides as therapeutic drugs. However, the common route of administration for the peptide drugs is limited to injection. Thus, a more simple preparation which can be administered by self-medication is desired, especially in the treatment of chronic disorders, to avoid the inconvenience of hospital treatment, and for the purpose of diminishing pain at the site of injection.

Recently, there have been many attempts to develop alternative administration, e.g. rectal, nasal, oral and etc., instead of injection. It has been found that even peptides, which are poorly absorbed in the form of a normal drug preparation, are promotedly absorbed by the addition of a surface active agent, and several absorption promotors have been found.

Among various physiologically active peptides now used as therapeutic drugs, calcitonins are generally known as peptide hormones having hypocalcemic activity inhibition of bone resorption and anti-ulcer actions, and are used clinically as therapeutic drugs for various conditions such as hypercalcemia, Paget's disease, and osteoporosis. It has been known that calcitonins are highly hydrophillic pepticles with a high molecular weight (as high as about 3,400) and are poorly absorbed through the gastrointestinal system. Accordingly, absorption through nasal mucosa using a nasal administration preparation with an absorption promotor has been tried, and such nasal administration preparations utilizing a surface active agent or a bile acid salt as the absorption promotor have been reported. For example, the Japanese Unexamined patent publication Nos. 89,619/1984 and 130,820/1984 disclosed the use of surface active agents. Using salmon calcitonin, H. Hanson et al reported in "Delivery system for Peptide Drugs, Plenum Press," (1986), pages 233–242 that the calcitonin which is poorly absorbed in the form of a normal preparation, is promotedly absorbed by addition of a surface active agent or bile acid.

However, these preparations are not satisfactory, due to inferior absorbability and local irritation and are not yet practically employed. Thus, absorption promotors having more absorption promoting effect and higher safety are desired.

Japanese Unexamined patent publication No. 238,261/1987 discloses that azacycloalkane derivatives exhibit superior absorption promoting effect. It was found that these derivatives have much stronger absorption promoting effect with physical properties different from those absorption promotors used in the conventional preparations for nasal administration. Accordingly, calcitonin preparations for nasal administration were prepared using such derivatives as the absorption promotor, but satisfactory results were not obtained since the emulsifiable agent required for emulsification, heretofore used, was ineffective.

Many studies have been conducted recently on emulsions which are liquid preparations containing water and oil in homogeneous state. Many emulsifying agents have been developed, and many stable emulsions have been broadly used, owing to significant progress in emulsifying techniques.

However, the majority of the emulsions are those using a nonionic surface active agent having a polyoxyethylene chain, or an ionic surface active agent, as the emulsifying agent, many of which are potentially toxic. Egg-yolk lecithin and soy bean lecithin commonly used as the emulsifying agent for fatty emulsions for intravenus injection. These emulsions are however, unstable and tend to separate at room temperatures.

The present invention has been accomplished in order to deal with such problems, and an object of the present invention is to provide a calcitonin emulsion preparation for nasal administration having excellent stability, when using an azacycloalkane derivative as the absorption promotor.

As the results of studies on emulsifying agents suitable to such emulsion preparations show, the present inventors have found that glycyrrhizic acid or its non-toxic salt, which has been thought to have low solvability are unexpectedly well suited for the emulsification of calcitonin nasal administration preparations using an azacycloalkane derivative as the absorption promotor, because they are stronger than nonionic surface active agents such as HCO-60 and Tween 80, thus yielding a stable emulsion with homogeneous fine particles.

Thus, the present invention relates to a calcitonin-containing emulsion for nasal administration, which is characterized by having a calcitonin as the active ingredient, and containing, at least, an azacycloalkane derivative of the general formula [1]:

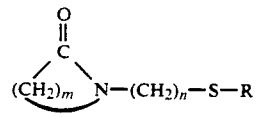

[1]

(wherein R is an alkyl residue, m is an integer of 2–4, and n is an integer of 1–15, provided that R is an alkyl residue with a carbon number of 5–11 in case where n is 1–3,) as the absorption promotor, glycyrrhizic acid or its non-toxic salt, and a suitable amount of water.

Calcitonins as the active ingredient in the present invention are commonly known as peptide hormones having hypocalcemic activity, inhibition of bone resorption and anti-ulcer activity. They are used clinically as therapeutic drugs for various hypercalcemia, Paget's disease, and osteoporosis. Naturally occurring calcitonins and their synthetic derivatives are known. Natural calcitonins include, for example eel calcitonin, salmon calcitonin, porcine calcitonin, human calcitoni, and chicken calcitonin. Synthetic calcitonis include, for example [ASU[1-7]] eel calcitonin (WHO generic name: elcatonin), [ASU[1-7]] chicken calcitonin, [ASU[1-7]] salmon calcitonin and [ASU[1-7]] human calcitonin. Elcatonin is the most preferred calcitonin for use in accordance with the present invention. Other calcitonin peptides having hypocalcernic activity may be employed in the present invention Typically, the calcitonin concentration in the calcitonin emulsions for nasal administration of this invention is 10–10,000 International Units, more preferably, 100–1,000 International Units, per milliliter of the preparation.

The azacycloalkane derivatives used as the absorption promoters in the present invention are oily materials, which are included in the above general formula [1] and illustrated in the Japanese Unexamined patent publication No. 238,261/1986. As embodiments of the R in the general formula [1], straight chain or branched alkyl residues, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicocyl, etc. may be mentioned. Among them, the preferred absorption promotor is 1-[2-(decylthio)ethyl]azacyclopentane-2-one (oil); R being an alkyl residue with a outon number of 10, $m = 3$ and $n = 2$, in the general formula [1].

The amount of such azacycloalkane derivative employed in the compositions of the present invention is preferably so as to give a concentration of 0.01%–10% (W/V), more preferably, 0.1%–5% (W/V).

Glycyrrhizic acid and its non-toxic salts, used in the present invention, are natural constituents extracted from licorice (Glycyrrhiza glabra), and widely used for cosmetics and food additives such as sweetening agents.

Examples of as the glycyrrhizic acid and its non-toxic salts, are glycyrrhizic acid, and dipotassium glycyrrhizate, monoammonium glycyrrhizate, disodium glycyrrhizate, trisodium glycyrrhizate, and the like. The concentration of these reagents in the compositions of this invention is normally at least. 0.1% (W/V), preferably 0.1%–5%, more preferably 0.5%–2%.

In general, preparations for nasal administration are aqueous liquid formulations either in spray or in drop form. The emulsions of the present invention may be prepared by using, the above-mentioned oily azacycloalkane derivative, glycyrrhizic acid or its non-toxic salt, and a suitable amount of water to give concentrations of the above constituents as mentioned above. They are preferably adjusted to a pH of 5–7 and an osmotic pressure ratio against physiological salt solution of about 1. To adjust or maintain pH 5–7, a pH adjusting agent such as sodium hydroxide, potassium hydroxide, sodium carbonate, sodium hydrogencarbonate, hydrochloric acid, sulfuric acid, or a buffer solution such as acetate, lactate, citrate and phosphate buffer solutions, may be added. To adjust the osmotic pressure ratio to approximately 1, an isotonic agent, preferably glycerol, may be used. If required, sodium chloride, potassium chloride, mannitol, glucose, and the like, may be added.

The compositions of the invention may also contain an, appropriate preservative such as a conventional pharmaceutically acceptable excipient, for example, p-oxybenzoate esters, chlorobutanol, phenylethyl alcohol, benzalkonium chloride, phenol, thimerosal, dehydroacetic acid, sorbic acid, and the like. Suitable concentration of such preservative is, generally, 0.02%–2% (W/V), varying depending on the agent selected.

Emulsions for nasal administration can be prepared by mixing each ingredient in an arbitrary sequence and emulsifying the mixture, according to well-known procedures. To prepare the emulsions of the present invention, for example, dipotassium glycyrrhizate, a calcitonin, and other related additives are added to a suitable amount of distilled water for injection purposes, and a solution is prepared by heating and agitation. Then, the solution is adjusted to a desired pH by addition of a pH adjustor, for example, sodium hydroxide or hydrochloric acid. After addition of an azacycloalkane derivative as the absorption promotor, the mixture may be emulsified by the conventional methods with an emulsifier. For example, use of Biomixer (NIHON SEIKI SEISAKUSHO) with 10,000 rpm agitation for 10 minutes yields a homogeneously dispersed emulsion with 0.1–0.3 μm fine particle size. An ultrasonic emulsifier and colloid mill, among others, may also be used for the preparation. Alternatiely, the calcitonin may be added after the preparation of the emulsion and allowed to dissolve. The resulting homogeneous calcitonin-containing emulsion preparation may be filtered under asepic conditions, for example, through a 0.22 μm membrane filter, and filled, for example, in vials to give the final product.

The dosage of the emulsion of the present invention varies depending on the purpose for which the composition is administrated but, in humans, the administration is secured by spraying the emulsion into a naris or nares using a metered-dose spray (0.05%–0.1 ml/stroke) one or two times per dose and 1–3 times a day.

One object of the calcitonin emulsion for nasal administration of the present invention is to administer the emulsion in the nasal cavity in the state of a mist using conventional spraying apparatus, thereby to secure a systemic effect. Using the preparation of the present invention, it is possible to administer calcitonin to the whole body through adhesion of the emulsion in the wide area of the nasal mucosa and substantial permeation through the mucosa. Accordingly, the calcitonin-containing emulsion for nasal administration of the present invention can be administered to patients having disorders needing treatment with calcitonins, even by the patients themselves, without the problems associated with injection.

The present invention will be more fully explained with respect to the following experimental and working examples, which are, however, not to be understood as limiting.

EXAMPLE 1

Stabilities of emulsions

<Experimental method>

Figure 1:
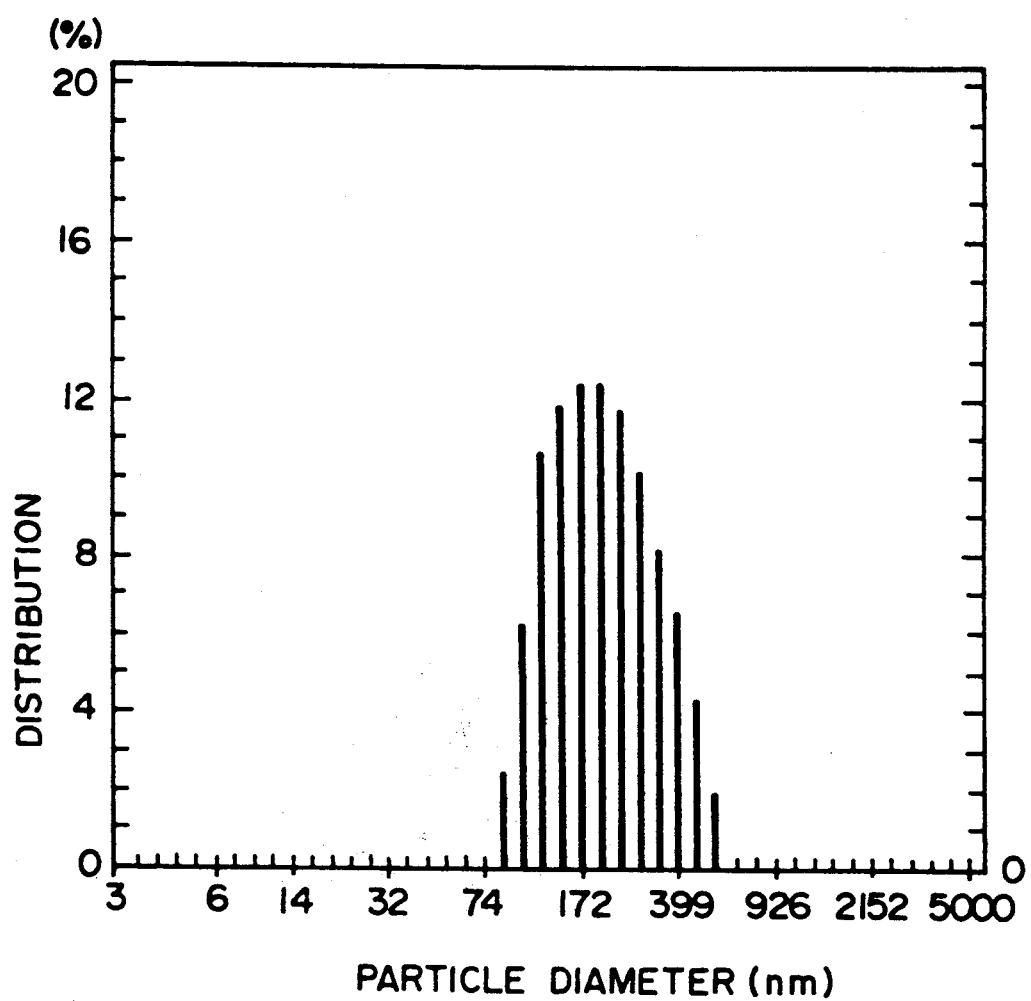
FIG. 1 shows average particle diameter and size distribution of the Preparation C prepared according to the present invention.

Using 1-[2-(decylthio)ethyl]azacyclopentan-2-one chosen from the azacycloalkane derivatives, and three emulsifying agents as follows, emulsifiabilities and stabilities of the emulsions were examined:

(1) Dipotassium glycyrrhizate (MARUZEN KASEI)
(2) HCO-60 (NIKKO Chemicals)
(3) Tween 80 (NIKKO Chemicals)

0.1 g of 1-[2-(decylthio)ethyl]azacyclo-pentan-2-one was placed in a test tube (10 ml), and thereto was added 5.0 ml of an aqueous solution prepared preliminarily by dissolving each of the above three emulsifying agents in a concentration of 0.1–0.5% (W/V), or water containing none of such agent. The mixture was agitated under 15,000 rpm for 1 minute by Biomixer (NIHON SEIKI SEISAKUSHO) to prepare each emulsion. The state of dispersion just after the preparation and after 3 days standing at room temperature was observed. The turbidity just after the preparation was measured by extinction at 650 nm, and used as the index of emulsifiability.

<Results>

The results are shown in Table 1–3. As obvious from the tables, dipotassium glycyrrhizate of the present invention exhibited good emulsification at 0.1–5% and gave full dissolution at 4–5%. The control which contained no dipotassium glycyrrhizate gave two phases which separated just after the preparation. Further, the stabilities of the emulsions after 3 days at room temperature were observed. Separation of the two phases were recognized in emulsions prepared using lower concentrations of HCO-60 and Tween 80.

As for the turbidity as the index of emulsifiability, dipotassium glycyrrhizate showed lower values, that is, stronger emulsifiability, than HCO-60 and Tween 80 when compared at the same concentration level. These results show that dipotassium glycyrrhizate is significantly superior in its emulsifiability and stability of the emulsion to HCO-60 and Tween 80 which are emulsifying agents widely used as additives for pharmaceuticals.

TABLE 1

| (Use of dipotassium glycyrrhizate) | | | |
|---|---|---|---|
| Concentrations (%) | Just after preparation | After 3 days standing | Turbidity* (650 μm) |
| 5.0 | Colorless clear | Colorless clear | 0.006 |
| 4.0 | Colorless clear | Colorless clear | 0.006 |
| 3.0 | White clear | White clear | 0.346 |
| 2.0 | White clear | White clear | 0.405 |
| 1.0 | White clear | White clear | 0.437 |
| 0.5 | White clear | White clear | 0.459 |
| 0.1 | White emulsified | White emulsified | 1.284 |
| Not added | Separated two phases | Separated two phases | — |

TABLE 2

| (Use of Tween 80) | | | |
|---|---|---|---|
| Concentrations | Just after preparations | After 3 days standing | Turbidity* (650 μm) |
| 5.0 | White clear | White clear | 0.172 |
| 4.0 | White clear | White clear | 0.165 |
| 3.0 | White clear | White clear | 0.244 |
| 2.0 | White clear | White clear | 0.803 |
| 1.0 | White emulsified | White emulsion separated | 1.119 |
| 0.5 | White emulsified | White emulsion separated | 2.619 |

TABLE 3

| (Use of HCO-60) | | | |
|---|---|---|---|
| Concentrations | Just after preparation | After 3 days standing | Turbidity* (650 μm) |
| 5.0 | White clear | White clear | 0.317 |
| 4.0 | White clear | White clear | 0.425 |
| 3.0 | White clear | White clear | 0.712 |
| 2.0 | White clear | White clear | 0.915 |
| 1.0 | White emulsified | White emulsion partially separated | 2.829 |
| 0.5 | White emulsified | White emulsion partially separated | 2.877 |

TABLE 3-continued

| (Use of HCO-60) | | | |
|---|---|---|---|
| Concentrations | Just after preparation | After 3 days standing | Turbidity* (650 μm) |
| | | separated | |

*Turbidity (650 μm) 0–0.1: colorless transparent 0.1–1.0: white transparent (backside visible when looking through) 1.0–: white emulsified (emulsion like commercially available milk)

Example 2

Stabilities of the emulsions relating to the added concentrations of the azacycloalkane derivative <Experimental method>

Each 5 ml of a 1% (W/V) solution preliminarily prepared by dissolving dispotassium glycyrrhizate in distilled water was poured in each of 8 10-ml-test tubes, and thereto was added 1[2-(decylthio)ethyl] azacyclopentan-2-one chosen from the azacycloalkane derivatives so as to make a concentration ranging from 0 to 10%. Then, the mixture was agitated for 1 minute using Biomixer (NIHON SEIKI SEISAKUSHO) (15,000 rpm), to prepare each emulsion. The state of dispersion just after the preparation, or after 3 days or 7 days standing at room temperature was observed.

<Results>

The results are shown in Table 4. As obvious from the table, using 1% dipotassium glycyrrhizate of the present invention, 1-[2-(decylthio)ethyl]azacyclopentan-2-one among the azacycloalkane derivatives at a concentration ranging from 0.01% to 10% exhibited good emulsification and gave a stable emulsion.

TABLE 4

| Stabilities of emulsions relating to the added concentrations of 1-[2-(decylthio)ethyl]azacyclopentan-2-one | | | |
|---|---|---|---|
| Concentrations (%) | Observation just after preparation | Observation after 3 days standing | Observation after 7 days standing |
| 10.0 | White emulsified | White emulsified | White emulsified |
| 5.0 | White emulsified | White emulsified | White emulsified |
| 2.0 | White clear | White clear | White clear |
| 1.0 | White clear | White clear | White clear |
| 0.5 | Colorless clear | Colorless clear | Colorless clear |
| 0.1 | Colorless clear | Colorless clear | Colorless clear |
| 0.01 | Colorless clear | Colorless clear | Colorless clear |
| 0 | Colorless clear | Colorless clear | Colorless clear |

| Ingredients per 1 ml of emulsion: | |
|---|---|
| elcatonin | 400 Units |
| 1-[2-(decylthio)ethyl]azacyclopentan-2-one | 20 mg |
| dipotassium glycyrrhizate | 10 mg |
| glycerol | 22 mg |
| methyl p-oxybenzoate | 1.0 mg |
| sodium hydroxide | to pH 6 |
| distilled water (for injection) | to make the volume 1 ml |

Control (a):

| Ingredients per 1 ml of emulsion: | |
|---|---|
| elcatonin | 400 Units |
| 1-[2-(decylthio)ethyl]azacyclopentan-2-one | 20 mg |
| HCO-60 | 10 mg |
| glycerol | 22 mg |

-continued

| | | |
|---|---|---|
| methyl p-oxybenzoate | 1.0 mg | |
| sodium hydroxide | to pH 6 | |
| distilled water (for injection) | to make the volume 1 ml | |
| Control (b): | | |
| Ingredients per 1 ml of emulsion: | | |
| elcatonin | 400 Units | |
| 1-[2-(decylthio)ethyl]azacyclopentan-2-one | 20 mg | |
| Tween 80 | 10 mg | |
| glycerol | 22 mg | |
| methyl p-oxybenzoate | 1.0 mg | |
| sodium hydroxide | to pH 6 | |
| distilled water (for injection) | to make the volume 1 ml | |

Emulsion compositions with the ingredients as mentioned above were prepared and subjected to severity tests. Appearances of the emulsions were examined and the contents of elcatonin were quantitated by HPLC method. The results are shown in Table 5. As obvious from the table, Controls (a) and (b) showed separation to two phases according to the lapse of time during the severity test at 50° C. The emulsion of the present invention was kept stable in the emulsified state for 3 months. It was also found that elcatonin in the emulsion of the present invention was maintained satisfactorily, compared to Controls (a) and (b).

TABLE 5

Stabilities of emulsions after 50° C. severity tests

| Examples | Tested items | Just after | 1 month | 2 months | 3 months |
|---|---|---|---|---|---|
| Composition of the invention | Appearance | White emulsion | White emulsion | White emulsion | White emulsion |
| | Residual ratio (%) | 100 | 96.2 | 93.8 | 87.4 |
| Control (a) | Appearance | White emulsion | White emulsion | Separated two phases | Separated two phases |
| | Residual ratio (%) | 100 | 87.4 | 82.2 | 76.3 |
| Control (b) | Appearance | White emulsion | Separated two phases | Separated two phases | Separated two phases |
| | Residual ratio (%) | 100 | 75.8 | 56.9 | 49.2 |

Example 4

Absorption test of beagles (1) Preparation of composition for nasal administration containing elcatonin ① Control preparation Ⓐ

Paraben solution: A Paraben solution was prepared in advance by adding 2.4 g of methyl p-oxybenzoate and 600 mg of propyl p-oxybenzoate in 2000 ml of distilled water for injection, and dissolving under agitation at 80° C.

Into a 500 ml-volume beaker was placed 100 ml of the Paraben solution. After adjusting the temperature to 40° C., 4.4 g of glycerol and 2 g of dipotassium glycyrrhizate were added thereto. After confirming the homogeneous dissolution, the solution was adjusted to pH 6.0 with 1 N sodium hydroxide, and then the volume was made up to 200 ml with the Paraben solution. After addition of 16 mg of elcatonin (specific activity, 5,446 Units/mg), the mixture was slowly agitated to make a solution, which was then filtered aseptically (with membrane filter of 0.22 μm) and filled aseptically into 3 ml vials adaptable to a mechanical spray for nasal administration to give the final preparation. This composition contained 400 Units/ml of elcatonin, and one stroke of the adapter accurately administered 40 Units.

② Preparation Ⓑ

Into a 500 ml-volume beaker was placed 100 ml of the Paraben solution prepared as above. After adjusting the temperature to 40° C., 4.4 g of glycerol and 2.0 g of dipotassium glycyrrhizate (MARUZEN KASEI) were added thereto. After confirming the homogeneous dissolution, 2.0 g of 1-[2-(decylthio)ethyl]azacyclopentan-2-one was added thereto, and the pH was adjusted to 6.0 with 1 N sodium hydroxide. Then, the total volume was made up to 200 ml with the Paraben solution as prepared above, followed by emulsification through agitation using Biomixer (NIHON SEIKI SEISAKUSHO Type ABM) generator shaft (BM-4) at 10,000 rpm for 5 minutes, thereby to obtain an emulsion. After addition of 16 mg of elcatonin (specific activity, 5,446 Units/mg), followed by slow agitation for dissolution, the resulting emulsion was aseptically filtered (with a membrane filter of 0.22 μm), and filled aseptically in each 3 ml vials adaptable to a mechanical spray for nasal administration, thereby to obtain the final preparation. This composition contained 400 Units/ml of elcatonin, and one stroke of the adapter accurately administered 40 Units.

③ Preparation Ⓒ

Using 4.0 g of 1-[2-(decylthio)ethyl] azacyclopentan-2-one and with otherwise the similar procedure to Preparation B, a preparation for nasal administration containing 400 Units/ml elcatonin was prepared.

④ Preparation Ⓓ

Using 6.0 g of 1-[2-(decylthio)ethyl] azacyclopentan-2-one and with otherwise the similar procedure to Preparation B, a preparation for nasal administration containing 400 Units/ml elcatonin was prepared.

⑤ Preparation Ⓔ

Using 10.0 g of 1-[2-(decylthio)ethyl] azacyclopentan-2-one and with otherwise the similar procedure to Preparation B, a preparation for nasal administration containing 400 Units/ml elcatonin was prepared.

(2) Average particle diameter and particle size distribution of the emulsion of the present invention Laser particle diameter analyzing system Using LPA-3000/3100 (OHTSUKA DENSHI KABUSHIKI KAISHA), the average particle diameter and particle size distribution of the Preparation C were examined. (The results are shown in FIG. 1.)

(3) Nasal administration tests to beagles

Male beagles (n=4), each weighing approximately 10 kg were used, and the present study was performed under non-anesthetized condition. Nasal administration was conducted by inserting a nozzle (hand made) for metered-dose spray for nasal administration into the nasal cavity of the dogs, and spray-administering 0.1 ml of the emulsion to each of both nares. As the control, a commercially available elcatonin-injection (40 Units) was intramuscularly injected (femoral region). Each 2.5 ml of the blood was collected in a heparinized syringe from the foreleg vein just before administration at intervals of 5, 10, 20, 30: 45, 60 and 120 minutes after administration of Elcatonin. After the collection, the plasma was separated by centrifugation (3,000 rpm) for 10 minutes, and was kept frozen at −30° C. until used for the assay. Elcatonin plasma level were evaluated by a RIA method, with a detection limit of 25 pg/ml.

(4) Results

① Average particle diameter and particle size distribution of the emulsions of the present invention A particle size distribution chart with respect to the Preparation C which is a typical example of the present invention is shown in FIG. 1, in which the average particle diameter is 192.3 μm. Thus, the present emulsion is found to have ideal particle diameter and size distribution as a nasal administration emulsion, when considering the stability and the nasal absorbability. Preparations B, D and E also exhibited ideal particle diameter and size distribution, while Control Preparation A remained in solution.

② Nasal administration tests to beagles

Figure 2:
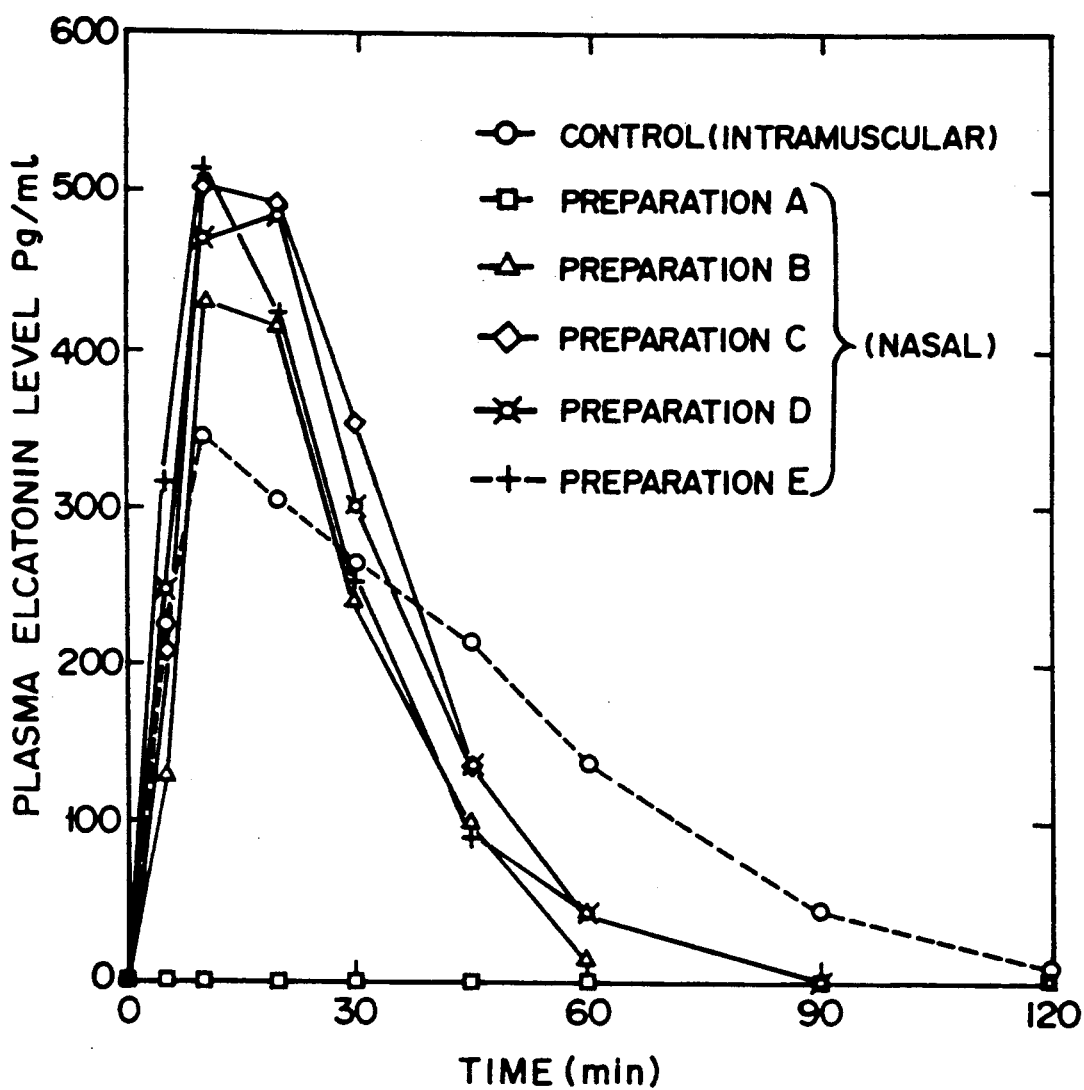
FIG. 2 shows elcatonin plasma levels versus time after nasal administration of elcatonin (80 units) to beagle dogs (n=4).

In the nasal administration of the emulsions of the present invention using elcatonin, the absorptions of the elcatonin in plasma are shown in FIG. 2. Comparison is made with the administration by intramuscular injection, which is shown by broken lines in the figure. Nasal administration of Control Preparation A without 1-[2-(decylthio) ethyl]azacyclopentan-2-one, a kind of azacycloalkane derivative showed plasma elcatonin level under the detection limit. Preparations B, C, D and E which contain 1-5% of 1-[2-(decylthio)ethyl]azacyclopentan-2-one exhibited much satisfactory absorptions. Thus, it is obvious that the emulsions of the present invention have significantly improved the nasal elcatonin absorbability when compared with Control Preparation A, and are proved to be a useful preparation in place of intramuscular administration, due to the superior biological availability.

In FIG. 2,

—— shows the results of intramuscularly administering elcatonin (40 Units/dog) as the control, —□— shows the results of nasal administration of control Preparation A (0%) obtained in ① of example 4, —△— shows the results of nasal administration of Preparation B (1%) obtained in ② of example 4, — — shows the results of nasal administration of Preparation C (2%) obtain in ③ of example 4, — — shows the results of nasal administration of Preparation D (3%) obtained in ④ of example 4, and —+— shows the results of nasal administration of Preparation E (5%) obtained in ⑤ of example 4.

Preferable working examples of the calcitonin emulsion for nasal administration of the present invention will be described below.

Example 5

Emulsions for nasal administration were prepared using the following amounts (per 1 ml) of ingredients:

| | | |
|---|---|---|
| ① | elcatonin each 100, 200 and 400 Units | |
| ② | 1-[2-(decylthio)ethyl] azacyclopentan-2-one | 10 mg |
| ③ | dipotassium glycyrrhizate | 10 mg |
| ④ | glycerol | 22 mg |
| ⑤ | benzalkonium chloride | 0.1 mg |
| ⑥ | sodium hydroxide | to pH 6 |
| ⑦ | distilled water for injection | a volume to make 1 ml |

The resulting eulsions were aseptically filtered (with a membrane filter of 0.22 μm), and aseptically filled in 3 ml vials adaptable to a mechanical spray for nasal administration, to obtain the final preparation. These compositions contained 100–400 Units/ml of elcatonin, and a stroke of the adapter accurately administered 10–40 Units.

Example 6

Emulsions for nasal administration were prepared using the following amounts (per 1 ml) of ingredients:

| | | |
|---|---|---|
| ① | elcatonin each 100, 200 and 400 Units | |
| ② | 1-[2-(decylthio)ethyl] azacyclopentan-2-one | 10 mg |
| ③ | dipotassium glycyrrhizate | 10 mg |
| ④ | sodium chloride | 8.0 mg |
| ⑤ | methyl p-oxybenzoate | 1.0 mg |
| ⑥ | sodium hydroxide | to pH 6 |
| ⑦ | distilled water for injection | a volume to make 1 ml |

The resulting emulsions were aseptically filtered (with a membrane filter of 0.22 μm), and aseptically filled in 3 ml vials adaptable to a mechanical spray for nasal administration, to obtain the final preparation. These compositions contained 200–400 Units/ml of elcatonin, and a stroke of the adapter accurately administered 20–80 Units.

Example 7

Emulsions for nasal administration were prepared using the following amounts (per 1 ml) of ingredients:

| | | |
|---|---|---|
| ① | elcatonin each 100, 200 and 400 Units | |
| ② | 1-[2-(decylthio)ethyl] azacyclopentan-2-one | 20 mg |
| ③ | monoammonium glycyrrhizate | 10 mg |
| ④ | sodium chloride | 8.0 mg |
| ⑤ | methyl p-oxybenzoate | 1.0 mg |
| ⑥ | sodium hydroxide | to pH 6 |
| ⑦ | distilled water for injection | a volume to make 1 ml |

The resulting emulsions were aseptically filtered (with a membrane filter of 0.22 μm), and aseptically filled in 3 ml vials adaptable to a mechanical spray for nasal administration, to obtain the final preparation. These compositions contained 100–400 Units/ml of elcatonin, and a stroke of the adapter accurately administered 10–40 Units.

Example 8

Emulsions for nasal administration were prepared using the following amounts (per 1 ml) of ingredients:

| | | |
|---|---|---|
| ① | Salmon calcitonin each 100, 200 and 400 Units | |
| ② | 1-[2-(decylthio)ethyl] azacyclopentan-2-one | 5 mg |
| ③ | dipotassium glycyrrhizate | 10 mg |
| ④ | glycerol | 22 mg |
| ⑤ | methyl p-oxybenzoate | 1.0 mg |

-continued

| | | |
|---|---|---|
| (6) | sodium hydroxide | to pH 6 |
| (7) | distilled water for injection | a volume to make 1 ml |

The resulting emulsions were aseptically filtered (with a membrane filter of 0.22 μm), and aseptically filled in 3 ml vials adaptable to a mechanical spray for nasal administration, to obtain the final preparation. These compositions contained 100–400 Units/ml of salmon calcitonin, and a stroke of the adapter accurately administered 10–40 Units.

In the present invention, homogeneous and stable emulsions for nasal administration containing calcitonins are produced by using an azacycloalkane derivative as the absorption promotor and glycyrrhizic acid or its non-toxic salt. The obtained emulsions exhibit satisfactory bio-availability with superior absorbability through nasal mucosa and less irritation to nasal mucosa, as compared to the conventional nasal administration preparations. Thus, practical use of calcitonin emulsions for nasal administration is made possible by the present invention.

We claim:

1. A calcitonin-containing emulsion for nasal administration, which is characterized by having a calcitonin as the active ingredient, and containing, at least, an azacycloalkane derivative of the general formula:

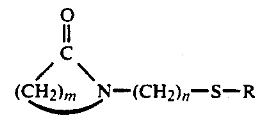

[1]

wherein R is an alkyl residue, m is an integer of 2–4 and n is an integer of 1–15, provided that R is an alkyl residue with a carbon number of 5–11 in case where n is 1–3 as the absorption promotor, glycyrrhizic acid or its non-toxic salt, and a suitable amount of water.

2. An emulsion according to claim 1 wherein the azacycloalkane derivative of the general formula is 1-[2-(decylthio)ethyl]-azacyclopentan-2-one (wherein R is an alkyl residue with a carbon number of 10, m is 3, and n is 2).

3. An emulsion according to c im 1 wherein the content of the calcitonin is 10–10,000 International Units per 1 ml of the emulsion.

4. An emulsion according to claim 1 wherein the amount of glycyrrhizic acid or its non-toxic salt is 0.1–5% (W/V) per emulsion.

5. An emulsion according to claim 1 wherein the amount of the azacycloalkane derivative is 0.01–10% (W/V) per emulsion.

6. An emulsion according to claim 1 wherein the calcitonin is elcatonin, the azacycloalkane derivative is 1-[2-(decylthio)ethyl]azacyclopentan-2-one and the glycyrrhizic acid or its non-toxic salt is dipotassium glycyrrhizate.

* * * * *

UNITED STATES PATENT AND TRADEMARK OFFICE
CERTIFICATE OF CORRECTION

PATENT NO. : 5,281,580
DATED : January 25, 1994
INVENTOR(S) : Nakayuki Yamamoto, et al It is certified that error appears in the above-identified patent and that said Letters Patent is hereby corrected as shown below:

On the title page: Item [75]

change: "Toyo Jozo Company, Ltd.; Hisamitsu Pharmaceutical Co., Inc., Saga Japan"

to read:--Asahi Kasei Kogyo Kabushiki Kaisha, Osaka, Japan--

Signed and Sealed this

Fourth Day of April, 1995

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,281,580
DATED : JANUARY 25, 1994
INVENTOR(S) : NAKAYUKI YAMAMOTO ET AL.

It is certified that error appears in the above-indentified patent and that said Letters Patent is hereby corrected as shown below:

On title page, item [73] change the
NAMES OF THE ASSIGNEES FROM "ASAHI KASEI KOGYO KABUSHIKI KAISHA" TO

-- ASAHI KASEI KOGYO KABUSHIKI KAISHA; HISAMITSU PHARMACEUTICAL CO., INC. --

Signed and Sealed this

Second Day of January, 1996

*Attest:*

BRUCE LEHMAN

*Attesting Officer*  *Commissioner of Patents and Trademarks*